US00PP25030P3

(12) United States Plant Patent
Suphachadiwong

(10) Patent No.: US PP25,030 P3
(45) Date of Patent: Nov. 4, 2014

(54) *PHALAENOPSIS* PLANT NAMED 'SUPHAL1309'

(50) Latin Name: ***Phalaenopsis* hybrid**
Varietal Denomination: SUPHAL1309

(71) Applicant: Thumrong Suphachadiwong, Chonburi (TH)

(72) Inventor: Thumrong Suphachadiwong, Chonburi (TH)

(73) Assignee: Suphachatawong Innovation (TH)

( * ) Notice: Subject to any disclaimer, the term of this patent is extended or adjusted under 35 U.S.C. 154(b) by 41 days.

(21) Appl. No.: 13/815,840

(22) Filed: Mar. 15, 2013

(65) Prior Publication Data

US 2014/0283264 P1 Sep. 18, 2014

(51) Int. Cl.
*A01H 5/00* (2006.01)

(52) U.S. Cl.
USPC ..... Plt./311

(58) Field of Classification Search
USPC ..... Plt./311
See application file for complete search history.

*Primary Examiner* — Kent L Bell
(74) *Attorney, Agent, or Firm* — Cassandra Bright

(57) ABSTRACT

A new and distinct *Phalaenopsis* cultivar named 'SUPHAL1309' is disclosed, characterized by small white flowers with yellow and white lip, small leaves and lateral sepals that are longer than the petals. The new variety is a *Phalaenopsis*, typically produced as an indoor ornamental plant.

2 Drawing Sheets

Figure 1:
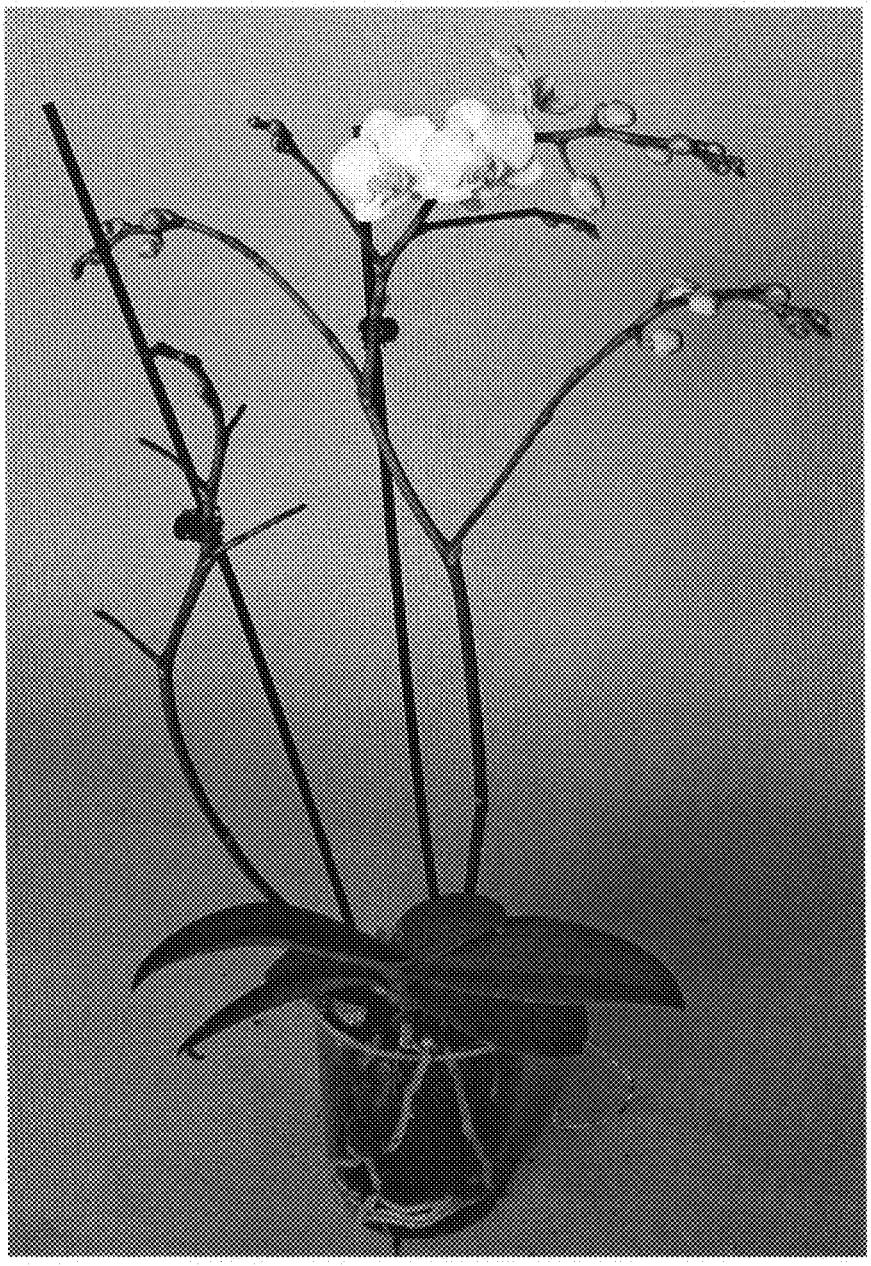

Latin name of the genus and species: *Phalaenopsis* hybrid. Variety denomination: 'SUPHAL1309'.

BACKGROUND OF THE INVENTION

This application relates to a new cultivar of *Phalaenopsis* hybrid. The new variety is the product of a planned breeding program. The new variety originated as a seedling from the crossing of the unpatented, proprietary seed parent *Phalaenopsis* 'WEQH7' with the unpatented, proprietary pollen parent referred to as *Phalaenopsis* 'TP17DIW'. The crossing was made by the inventor in his research greenhouse in Chonburi, Thailand in September of 2005.

The new variety was first selected by the inventor, Thumrong Suphachadiwong, a citizen of Thailand, in October of 2008 in a research greenhouse belonging to the inventor in Chonburi, Thailand. After identifying the new variety as a potentially interesting selection, the inventor continued confidential testing and propagation of 'SUPHAL1309', assessing stability of the unique characteristics of this variety.

Asexual reproduction of the new cultivar 'SUPHAL1309' was first performed at a commercial laboratory belonging to the inventor in Chonburi, Thailand by tissue culture in June of 2009. Access to all plants was restricted, as plants were kept in a greenhouse not open to the public, and tissue culture plantlets were in a laboratory belonging to the inventor, and not accessible to the public. Through subsequent propagation, multiple generations have been reproduced, which have shown that the unique features of this cultivar are stable and reproduced true to type.

SUMMARY OF THE INVENTION

The cultivar 'SUPHAL1309' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SUPHAL1309'. These characteristics in combination distinguish 'SUPHAL1309' as a new and distinct *Phalaenopsis* cultivar:

1. Small white flowers with yellow and white lip.
2. Small leaves.
3. Lateral sepals are longer than petals.

PARENT COMPARISON

Plants of the new cultivar 'SUPHAL1309' are similar to the seed parent, *Phalaenopsis* 'WEQH7' in most horticultural characteristics. The new variety, however, grows faster than the seed parent. Additionally, the new variety produces larger flowers with a darker yellow lip than the seed parent.

Plants of the new cultivar 'SUPHAL1309' are similar to the pollen parent, *Phalaenopsis* 'TP17DIW' in most horticultural characteristics. Plants of the new variety however produce more compact and rounder flowers than the pollen parent. Additionally the new variety produces a more compact plant than the pollen parent.

COMMERCIAL COMPARISON

'SUPHAL1309' is similar to the unpatented commercial variety *Phalaenopsis* 'Angel' in most horticultural characteristics. However the new variety, 'SUPHAL1309' differs from 'Angel' in the following characteristics:

1. Different apical lobe shape.
2. Lateral sepals are longer than petals, which is the opposite of 'Angel'.
3. Smaller flowers.
4. Pink blush on back side of sepals and petals.

'SUPHAL1309' is similar to the unpatented commercial variety *Phalaenopsis* 'Flour Cloud' in most horticultural characteristics. However the new variety, 'SUPHAL1309' differs from 'Flour Cloud' in the following characteristics:

1. Shorter leaves.
2. Lateral sepals are longer than petals, which is the opposite of 'Flour Cloud'.
3. Different apical lobe shape.
4. Yellow coloration of the callus not found on 'Flour Cloud'.

BRIEF DESCRIPTION OF THE PHOTOGRAPH

The accompanying photographs in FIG. 1 illustrates in full color a typical plant of 'SUPHAL1309' grown in a commercial greenhouse in Zuidbroek, the Netherlands. This plant is approximately 18 months old after deflasking, shown planted in an 11 cm container.

Figure 2:
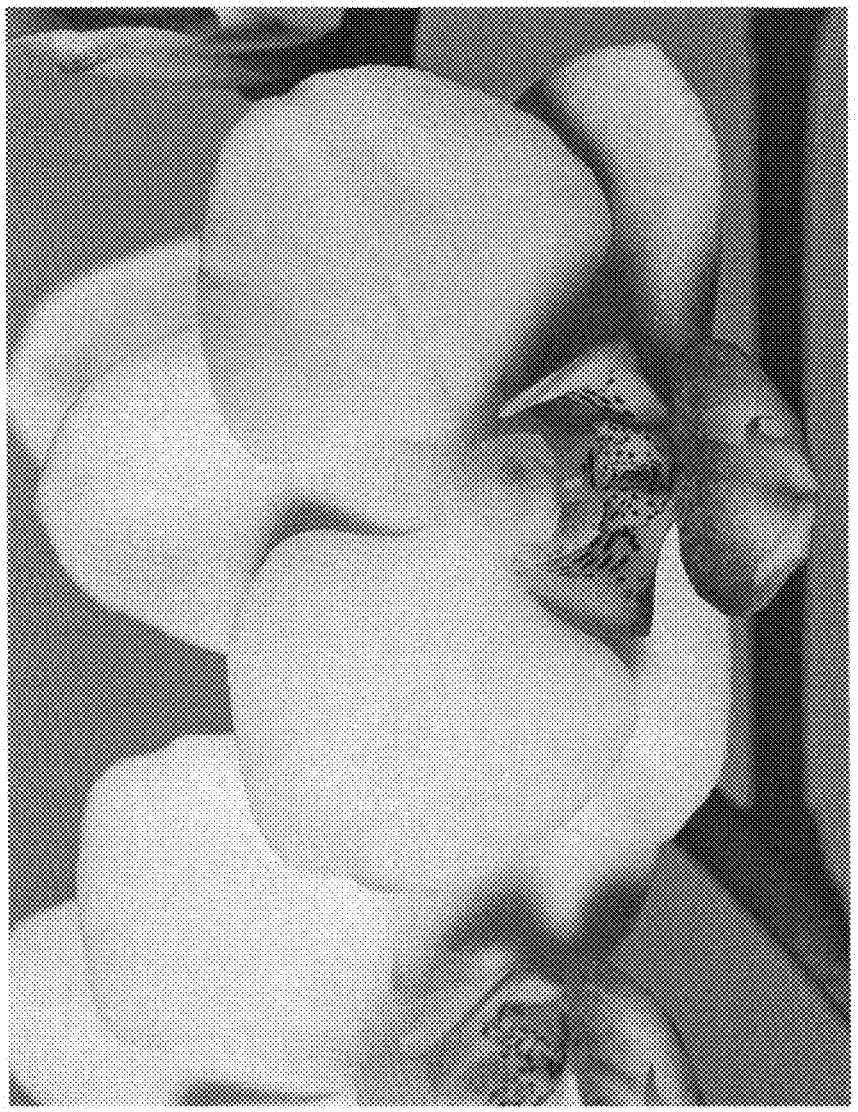

FIG. 2 illustrates a close up of the individual flower.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'SUPHAL1309' plants grown in a commercial greenhouse in Zuidbroek, the Netherlands. This plant is approximately 18 months old after deflasking, shown planted in an 11 cm container. Temperatures ranged between 18° C. and 28° C. day and night. No photoperiodic or chemical treatments were given to the plants. During bright Summer conditions, shade was given. During dark Winter months, supplemental light was given at unspecified amounts. Measurements and numerical values represent averages of typical plant types.

Botanical classification: *Phalaenopsis* hybrid 'SUPHAL1309'.

PROPAGATION

Type of propagation typically used: Tissue culture.

Time to initiate roots: About 21 days at approximately 28° C.

Time to produce a rooted cutting/liner: About 26 weeks at approximately 18° C. to 28° C.

Root description: Thick (typical for *Phalaenopsis*) and rounded, average diameter: 5 mm, colored greyed-green; near RHS 194A to 194B.

PLANT

Growth habit: Monopodial.

Height from top of soil line to top of foliage: Average 6.6 cm.

Height from top of soil line to top of flowers: Average 44.4 cm.

Plant spread: At widest, average: 35.0 cm; at narrowest: 11.5 cm.

Normal pot size: 11 cm.

Growth rate: Moderate.

Number of leaves per plant: Average 6.

FOLIAGE

Leaf:

*Arrangement*.—Distichous.

*Average length*.—Approximately 12.6 cm (including sheath).

*Average width*.—Approximately 5.3 cm.

*Shape of blade*.—Obovate to elliptic.

*Aspect*.—Horizontal.

*Apex*.—Unequal acute.

*Base*.—Cuneate. Sheath length: Average 1.3 cm. Sheath width: Average 1.2 cm. Sheath color: Green; near RHS 143C.

*Margin*.—Entire.

*Texture of top surface*.—Smooth, very slightly furrowed.

*Texture of bottom surface*.—Smooth.

*Appearance*.—Glossy all surfaces.

*Color*.—Young foliage upper side: Yellow-green; near RHS 146A. Young foliage under side: Yellow-green; near RHS 146A. Mature foliage upper side: Green to yellow-green; in between RHS 143A and 146A. Mature foliage under side: Yellow-green; near RHS 146B.

*Venation*.—Type: Camptodromous. Venation coloration: upper side green to yellow-green; in between RHS 143A and 146A, under side yellow-green; near RHS 146B, main vein on under side green; near RHS 143A.

Petiole: No petiole present.

FLOWERING CHARACTERISTICS

Flower bud:

*Rate of opening*.—Approximately 3 days after stage described.

*Length*.—Approximately 1.5 cm.

*Diameter*.—Approximately 1.4 cm wide and 1.4 cm high.

*Shape*.—Broad ovate.

*Color*.—Yellow-green; near RHS 140D, upper side tinged red-purple; near RHS 63A, 63B and 63C.

Peduncle:

*Length*.—Approximately 50.5 cm.

*Width*.—Approximately 0.5 cm.

*Aspect*.—Approximately 50° angle to rosette.

*Strength*.—Strong.

*Texture*.—Smooth.

*Appearance*.—Matte.

*Color*.—Yellow-green; near RHS 148A, finely dotted yellow-green; near RHS 144B.

Inflorescence:

*Flowers per stem*.—Average 35.

*Inflorescence arrangement*.—Compound panicle.

*Inflorescence height*.—Approximately 29.3 cm (measured from lowest branching of panicle to top of inflorescence).

*Inflorescence width*.—Approximately 34.0 cm.

Individual flowers:

*Flower type*.—Single zygomorphic flower.

*Shape*.—Rounded deltate.

*Length* (*height*).—Approximately 4.6 cm.

*Width*.—Approximately 4.3 cm.
*Depth*.—Approximately 2.2 cm.
*Fragrance*.—No fragrance.
*Persistent*.—Non-persistent.
*Quantity of petals*.—2 true petals.

Petals:
*Arrangement*.—One petal on each side of the column.
*Length*.—Approximately 2.3 cm.
*Width*.—Approximately 2.6 cm.
*Shape*.—Deltoid.
*Apex*.—Rounded.
*Base*.—Cuneate.
*Margin*.—Entire.
*Texture*.—Upper (forward) surface: Smooth, moderately velvety.
*Texture*.—Lower (back) surface: Smooth, moderately velvety.
*Appearance*.—Matte all surfaces.
*Color*.—When opening, forward surface: White; near RHS NN155C. When opening, back surface: White; near RHS NN155C with a purple central band; base purple; near RHS 76C. Fully Opened, forward surface: White; near RHS NN155C. Fully Opened, back surface: White; near RHS NN155C with a purple central band; base purple; near RHS 76C. Fading, forward surface: Not fading, only becoming non-velvety. Fading, back surface: Not fading, only becoming non-velvety.
*Color venation*.—Fully Opened, forward surface: As surface, white; near RHS NN155C. Fully Opened, back surface: As surface, white; near RHS NN155C, with a purple central band; base purple; near RHS 76C, main vein very slightly darker than central band; in between RHS 76B and 76C.

Labellum:
*Shape*.—Three-parted.
*Length*.—Approximately 1.9 cm.
*Width*.—Approximately 1.7 cm.
*Texture*.—Smooth, slightly velvety.
*Appearance*.—Matte.
*Tip*.—Cleft, tips cirrhose, curled upward.
*Base*.—Cuneate.
*Color*.—When opening, forward surface: Central lobe white; near RHS NN155D, base yellow; near RHS 13B, finely marbled yellow-orange; near RHS 22A, lateral lobes white; near RHS NN155D, base dotted red-purple; near RHS 61A, lower margin yellow; 13B, callosities yellow; near RHS 8B, dotted red-purple; near RHS 61A. When opening, back surface: Central lobe white; near RHS NN155D, margins on upper half yellow; near RHS 13C, lateral lobes white; near RHS NN155D, lower margin yellow; 13B. Fully Opened, forward surface: Central lobe white; near RHS NN155D, base yellow; near RHS 13B, finely marbled yellow-orange; near RHS 22A, lateral lobes white; near RHS NN155D, base dotted red-purple; near RHS 61A, lower margin yellow; 13B, callosities yellow; near RHS 8B, dotted red-purple; near RHS 61A. Fully Opened, back surface: Central lobe white; near RHS NN155D, margins on upper half yellow; near RHS 13C, lateral lobes white; near RHS NN155D, lower margin yellow; 13B. Fading, forward surface: Not fading, only becoming non-velvety. Fading, back surface: Not fading, only becoming non-velvety.
*Color venation*.—Fully Opened, forward surface: Main vein of central lobe yellow; near RHS 5D, no other venation visible. Fully Opened, back surface: No venation visible.
*Margin*.—Entire.

Sepals:
*Quantity*.—3.
*Length*.—Dorsal sepal approximately 2.5 cm. Lateral sepals approximately 2.3 cm.
*Width*.—Dorsal sepal approximately 2.1 cm. Lateral sepals approximately 1.95 cm.
*Shape*.—Ovate.
*Apex*.—Broad bluntly acute to obtuse.
*Base*.—Broad cuneate.
*Margin*.—Entire.
*Texture*.—Smooth, moderately velvety.
*Appearance*.—Matte.
*Color*.—Fully Opened, forward surface: White; near RHS NN155D, lateral sepals sparsely and finely dotted purple at the base; near RHS 77B. Fully Opened, back surface: White; near RHS NN155D, tinged purple; near RHS N74D and with a small purple spot near the top; near RHS N74C.

Pedicels:
*Length*.—Approximately 2.4 cm.
*Diameter*.—Approximately 0.2 cm.
*Angle*.—Approximately 85° to peduncle.
*Strength*.—Moderately strong.
*Texture*.—Smooth.
*Appearance*.—Moderately glossy.
*Color*.—Basal part yellow-green; near RHS 145C and 145D, central part white; N155B, distal part purple; near RHS 75C.

REPRODUCTIVE ORGANS

*Stamens, style and stigma fused into column?*.—Yes.
*Column length*.—Approximately 0.9 cm.
*Column diameter*.—Approximately 0.6 cm.
*Column color*.—White; near RHS NN155C to NN155D.
*Ovary*.—Position: Inferior. Diameter: Approximately 0.3 cm. Color: White; near RHS NN155C to NN155D.
*Pollen color*.—Yellow-orange; near RHS 23A.

OTHER CHARACTERISTICS

Disease resistance: Neither resistance nor susceptibility to the normal diseases found in *Phalaenopsis* has been observed.
Drought tolerance and cold tolerance: Normal for species.
Fruit/seed production: No fruits/seeds detected to date.

What is claimed is:

1. A new and distinct cultivar of *Phalaenopsis* plant named 'SUPHAL1309' as herein illustrated and described.

* * * * *